United States Patent [19]
Askin et al.

[11] Patent Number: 6,160,118
[45] Date of Patent: Dec. 12, 2000

[54] PROCESS FOR THE SYNTHESIS OF SUBSTITUTED PIPERAZINONES VIA MITSUNOBU REACTION

[75] Inventors: David Askin, Warren, N.J.; Stephanie Lewis, Coventry, N.Y.; Steven A. Weissman, Short Hills, N.J.

[73] Assignee: Merck & Co., Inc., Rahway, N.J.

[21] Appl. No.: 09/338,643

[22] Filed: Jun. 23, 1999

Related U.S. Application Data

[60] Provisional application No. 60/091,420, Jul. 1, 1998.

[51] Int. Cl.$^7$ .................... C07D 401/06; C07D 241/08
[52] U.S. Cl. ............................ 544/370; 544/384
[58] Field of Search ...................... 544/370, 384

[56] References Cited

U.S. PATENT DOCUMENTS

| | | | |
|---|---|---|---|
| 3,365,453 | 1/1968 | Archer et al. | 544/384 |
| 4,772,705 | 9/1988 | Schmiesing | 544/344 |
| 5,856,326 | 1/1999 | Anthony et al. | 544/370 X |
| 5,885,995 | 3/1999 | Dinsmore | 544/370 X |

OTHER PUBLICATIONS

Org. Reactions, 42 (1992), p. 335–656, by D. L. Hughes.
Heterocycles, vol. 29, No. 2 (1989), pp. 359–363, by J. Schmiesing, et al.
Tetrahedron Letters, vol. 35, No. 51 (1994), pp. 9545–9548, by A. Benjahad, et al.
J. Med. Chem., vol. 38 (1995), pp. 923–933, by R. T. Lewis, et al.
J. Chem. Soc., Perkin Trans. Part 1 (1997), pp. 503–509, by P. S. Hadfield, et al.
J. Org. Chem, vol. 57 (1992), pp. 6257–6265, by G. S. Poindexter, et al.
J. Org. Chem., vol. 42 (1977), pp. 4035–4040, by G. E. Struve, et al.
J. Org. Chem., vol. 62 (1997), pp. 1016–1022, by A. Pohlmann, et al.
Int. J. Pharm., vol. 146 (1997), pp. 147–157, by S. Takada, et al.
Biochem. Pharmacol., vol. 34, No. 3 (1985), pp. 393–394, by S. Caccia, et al.
Bioorg. Med. Chem. Letters, vol. 4, No. 7 (1994), pp. 867–872, by A. R. Batt, et al.
Tetrahedron Letters, vol. 39 (1998), pp. 7459–7462, by S. A. Weissman, et al.
J. Am. Chem. Soc., vol. 62 (1940), pp. 1202, by S. Aspinall, et al.
Synthesis (1984), pp. 969–970, by J. G. Pfister.
Tetrahedron Letters, vol. 48, No. 23 (1992), pp. 4985–4908 (1992), by S. Jain, et al.
Tetrahedron Letters, vol. 35, No. 16, pp. 2533–2536 (1994), by V. Schanen, et al.
Pharmazie, vol. 44 (1989), pp. 643, by B. Cossec, et al.
Tetrahedron Letters, vol. 39 (1998), pp. 221–224, by K. Shreder, et al.
Tetrahedron Letters, vol. 35, No. 5, pp. 673–676 (1994), by D. Askin et al.
J. Am. Chem. Soc., vol. 112 (1990), pp. 760–770, by G. M. Salituro, et al.
Synthesis 1981, 1–28 by O. Mitsunobu.
Organic Synthesis, vol. 42, pp. 19–22 (1962), by J. C. Craig, et al.
Hughes, D.L., "Progress in the Mitsunobu Reaction, A Review," Org. Prep. Proced. Int., vol. 28 (2), pp. 127–164 (1996).

*Primary Examiner*—Fiona T. Powers
*Attorney, Agent, or Firm*—Dianne Pecoraro; Mark R. Daniel

[57] ABSTRACT

The present invention is directed to a process for synthesizing substituted piperazinones, which are useful intermediates for making farnesyl-protein transferase inhibitors, using a Mitsunobu reaction.

33 Claims, No Drawings

PROCESS FOR THE SYNTHESIS OF SUBSTITUTED PIPERAZINONES VIA MITSUNOBU REACTION

This application claims benefit to Provisional Application 60/091420 filed Jul. 1, 1998.

BACKGROUND OF THE INVENTION

The Ras proteins are a family of guanine nucleotide binding GTPases that play a pivotal role in mediating cell growth, differentiation and development. (Barbacid, *Annual Review of Biochemistry*, Vol. 56, p. 779 (1987)). In mammalian cells, there are three ras genes that encode four Ras proteins, H, N, KA and KB-Ras. (E. C. Lerner et al., *Anti-Cancer Drug Design*, Vol. 12, pp. 229–238 (1997)). Mutations in Ha-ras, Ki-ras and N-ras, and the overexpression of Ras has been observed in approximately 30% of all human cancer tissues. (Lerner et al., S. L. Graham, *Exp. Opin. Ther. Patents*, Vol. 5, no. 12, pp. 1269–1285 (1995); T. Hiwasa, *Oncology Reports*, Vol. 3, pp. 7–14 (1996); S. L. Graham and T. M. Williams, *Exp. Opin. Ther. Patents*, Vol. 6, no. 12, pp. 1295–1304 (1996)). Although several steps are involved in modifying Ras proteins, farnesylation is the only step which is required and sufficient for Ras transforming activity. (E. C. Lerner et al.) Therefore, farnesyl-transferase (FTase) serves as an attractive target for the development of a potential new class of anti-cancer agents. (E. C. Lerner et al.) It has been noted that routes to inhibitors of Ras farnesylation are apparent from an examination of the substrate specificities of the enzyme. One can design analogs either of the lipid, or of the peptide sequence to which the lipid is transferred. Such compounds must be stable, and readily cross the cell membrane to gain access to the cytosolic transferase. (J. E. Buss and J. C. Marsters, Jr., *Chemistry and Biology*, Vol. 2, pp. 787–791 (1995)).

Compounds that incorporate substituted-piperazinone moieties have been observed to be farnesyltransferase inhibitors (WO 96/30343, published on Oct. 30, 1996). It is therefore desirable to discover a process for making substituted piperazinones that is efficient and operationally facile. Many prior syntheses for 1-aryl-piperazinones have required a 5-step procedure. Syntheses previously described require multiple isolation steps and high temperatures for installation of an ethylamine equivalent. These processes have also utilized expensive reagents. The overall yield from the previously described syntheses are typically less than 50%. Other processes useful for synthesizing beta-lactams from a hydroxyamine in the presence of a tertiary amine have been described. However, such a synthesis is dependent on the amine being tertiary, or protected, and not secondary or primary, to avoid competing aziridine formation. (G. M. Salituro et al., *J. Am. Chem. Soc.* 1990, Vol. 112, pp. 760–770). There is an example of the synthesis of a bicyclic piperazinone via a Mitsunobu reaction in the presence of a protected tertiary amine. (P. S. Hadfield et al., *J. Chem. Soc., Perkins Trans.* 1, 1997, pp. 503–509). Typically, the products synthesized via a Mitsunobu reaction require purification via column chromatography. Column chromatography has been used in such instances to separate the reaction product from the phosphine oxide and hydrazine by-products. (D. Hughes, *Organic Reactions*, Vol. 42, pp 335–656, (1992)). It is therefore desirable to design a process which isolates and purifies the synthesized compounds in one step, without the use of column chromatography.

It is therefore an object of this invention to provide a process for the synthesis of substituted piperazinones that is less time-consuming and more efficient.

It is a further object of this invention to provide a process for the synthesis of substituted piperazinones that employs readily available reagents and uses tertiary amines which are not protected.

It is a further object of this invention to provide a process for the synthesis of substituted piperazinones that synthesizes the compounds via cyclodehydration in the presence of secondary amines.

It is a further object of this invention to provide a process for the synthesis of substituted piperazinones that results in an overall yield which is higher than 50%.

SUMMARY OF THE INVENTION

The present invention is directed to the improved synthesis of compounds, as illustrated by formula I, which are useful in the synthesis of farnesyl-protein transferase inhibitors:

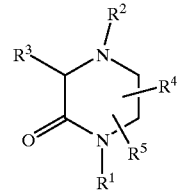

I

The process of the instant invention requires less time and is more efficient than syntheses previously disclosed. This process uses, in particular, the cyclodehydration of hydroxyamides, under Mitsunobu conditions, to obtain the piperazinone compounds of formula I.

DETAILED DESCRIPTION OF THE INVENTION

The present invention is a novel process for the synthesis of compounds as illustrated by formula I:

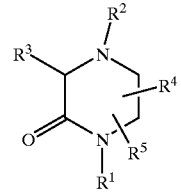

I wherein
$R^1$ is selected from
  a) H,
  b) unsubstituted or substituted $C_1$–$C_6$ alkyl,
  c) unsubstituted or substituted aryl,
  d) unsubstituted or substituted heteroaryl,
  e) —$R^a$C(O)OR, or
  f) —$R^a$ SR;
$R^2$, $R^3$, $R^4$ and $R^5$ are independently selected from:
  a) H,
  b) unsubstituted or substituted $C_1$–$C_6$ alkyl;
  c) unsubstituted or substituted aryl,
  d) unsubstituted or substituted heteroaryl,
  e) unsubstituted or substituted aralkyl,
  f) unsubstituted or substituted heteroaralkyl, g) unsubstituted or substituted $C_1$–$C_6$ alkoxy,
h) $C_1$–$C_6$ alkynyl;
i) $CF_3$, and
j) $OCF_3$;
$R^a$ is independently selected from
  a) unsubstituted or substituted —$(CH_2)_{1-6}$—;
  b) unsubstitued or substituted aryl, or
  c) unsubstituted or substituted aralkyl;
R is independently selected from
  a) unsubstituted or substituted $C_1$–$C_6$ alkyl,
  b) unsubstituted or substituted aryl, or
  c) unsubstituted or substituted aralkyl;
or the pharmaceutically acceptable salts thereof;
which comprises the steps of:
  a) acylating an unsubstituted or substituted amine using an acylating agent of formula II

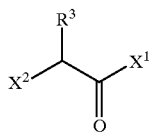

II (where $X^1$ is selected from halo, OH or unsubstituted or substituted $C_1$–$C_6$ alkoxy; $X^2$ is selected from halo or unsubstituted or substituted sulfonate and $R^3$ is as defined above) and a base compound;
  b) adding an amino alcohol of formula III

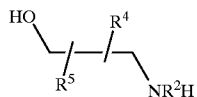

III (where $R^2$, $R^4$ and $R^5$ are as defined above) to produce a reaction mixture containing an amide alcohol of formula A:

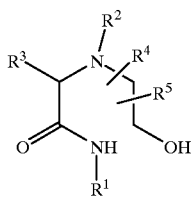

A (where $R^1$, $R^2$ $R^3$ $R^4$ and $R^5$ are as defined above);
  c) adding a phosphine and adding an azodicarboxamide or an azodicarboxylate; and
  d) isolating a compound of the formula I.

A further embodiment of the instant invention is the process hereinabove where an azodicarboxamide is added in step c).

Another embodiment of the instant invention is the process hereinabove where an azodicarboxylate is added in step c).

In second embodiment of the instant invention, the process for the synthesis of compounds as illustrated by formula I:

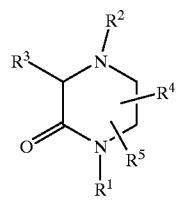

I wherein
$R^1$ is selected from
  a) H,
  b) unsubstituted or substituted $C_1$–$C_6$ alkyl,
  c) unsubstituted or substituted aryl,
  d) unsubstituted or substituted heteroaryl,
  e) —$R^aC(O)OR$, or
  f) —$R^aSR$;
$R^2$, $R^3$, $R^4$ and $R^5$ are independently selected from:
  a) H,
  b) unsubstituted or substituted $C_1$–$C_6$ alkyl;
  c) unsubstituted or substituted aryl,
  d) unsubstituted or substituted heteroaryl,
  e) unsubstituted or substituted aralkyl,
  f) unsubstituted or substituted heteroaralkyl,
  g) unsubstituted or substituted $C_1$–$C_6$ alkoxy,
  h) $C_1$–$C_6$ alkynyl;
  i) $CF_3$, and
  j) $OCF_3$;
R is independently selected from
  a) unsubstituted or substituted $C_1$–$C_6$ alkyl,
  b) unsubstituted or substituted aryl, or
  c) unsubstituted or substituted aralkyl;
$R^a$ is independently selected from:
  a) unsubstituted or substituted —$(CH_2)_{1-6}$—,
  b) unsubstituted or substituted aryl,
  c) unsubstituted or substituted aralkyl;
or the pharmaceutically acceptable salts thereof;
comprises the steps of:
  a) acylating an unsubstituted or substituted amine using an acylating agent of formula II

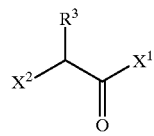

II (where $X^1$ is selected from halo, OH or unsubstituted or substituted $C_1$–$C_6$ alkoxy; $X^2$ is selected from halo or unsubstituted or substituted sulfonate and $R^3$ is as defined above) and an inorganic base compound to produce an acylated product;
  b) adding the acylated product to an amino alcohol of formula III

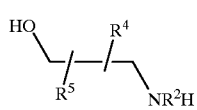 III (where $R^2$, $R^4$ and $R^5$ are as defined above) to produce a reaction mixture containing an amide alcohol of formula A

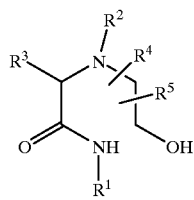 A (where $R^1$, $R^2$ $R^3$ $R^4$ and $R^5$ are as defined above);
c) adding a phosphine and adding an azodicarboxamide or an azodicarboxylate; and
d) isolating a compound of the formula I.

In a further embodiment of the instant invention, the process for synthesizing compounds of formula IA

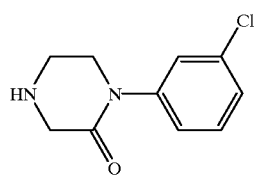 IA comprises the steps of:
a) acylating 3-chloroaniline with chloroacetylchloride and aqueous potassium bicarbonate;
b) adding ethanolamine to produce a reaction mixture containing an amide alcohol;
c) adding tributyl phosphine and a dipiperidineazodicarbonyl; and
d) isolating a compound of formula IA.

In a further embodiment of the instant invention, the process for synthesizing compounds of formula IA

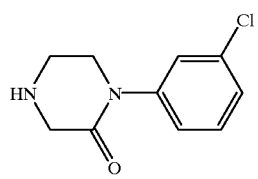 IA comprises the steps of:
a) acylating 3-chloroaniline with chloroacetylchloride and aqueous potassium bicarbonate;
b) adding ethanolamine to produce a reaction mixture containing an amide alcohol;
c) adding tributyl phosphine and a diisopropylazodicarboxylate; and
d) isolating a compound of formula IA.

In third embodiment of the instant invention, the process for the synthesis of compounds as illustrated by formula I:

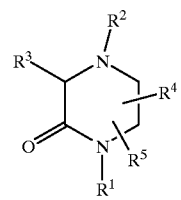 I wherein
$R^1$ is selected from
a) H,
b) unsubstituted or substituted $C_1$–$C_6$ alkyl,
c) unsubstituted or substituted aryl,
d) unsubstituted or substituted heteroaryl,
e) —$R^a$C(O)OR, or
f) —$R^a$SR;
$R^2$, $R^3$, $R^4$ and $R^5$ are independently selected from:
a) H,
b) unsubstituted or substituted $C_1$–$C_6$ alkyl;
c) unsubstituted or substituted aryl,
d) unsubstituted or substituted heteroaryl,
e) unsubstituted or substituted aralkyl,
f) unsubstituted or substituted heteroaralkyl,
g) unsubstituted or substituted $C_1$–$C_6$ alkoxy,
h) $C_1$–$C_6$ alkynyl;
i) $CF_3$, and
j) $OCF_3$;
R is independently selected from
a) unsubstituted or substituted $C_1$–$C_6$ alkyl,
b) unsubstituted or substituted aryl, or
c) unsubstituted or substituted aralkyl;
$R^a$ is independently selected from:
a) unsubstituted or substituted —$(CH_2)_{1-6}$—;
b) unsubstituted or substituted aryl,
c) unsubstituted or substituted aralkyl;
or the pharmaceutically acceptable salts thereof;
which comprises the steps of:
a) acylating an unsubstituted or substituted amine using an acylating agent of formula II

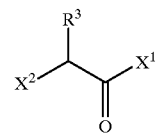 II (where $X^1$ is selected from halo, OH or unsubstituted or substituted $C_1$–$C_6$ alkoxy; $X^2$ is selected from halo or unsubstituted or substituted sulfonate and $R^3$ is as defined above) and a inorganic base compound to produce an acylated product;

b) adding an amino alcohol of formula III

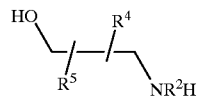

III (where $R^2$, $R^4$ and $R^5$ are as defined above) to the acylated product to produce a reaction mixture;

c) mixing a phosphine and adding an azodicarboxylate or an azodicarboxamide to produce a reagent mixture;

d) adding the reagent mixture from step c) to the reaction mixture of step b);

e) isolating a compound of formula I.

A further embodiment of the instant invention is the process hereinabove where, in step b), the acylated product is added to the amino alcohol of formula III to produce a reaction mixture.

In a further embodiment of the instant invention, the process for synthesizing compounds of formula IA

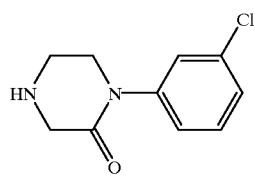

IA comprises the steps of:

a) acylating 3-chloroaniline with chloroacetylchloride and aqueous potassium bicarbonate;

b) adding ethanolamine to produce a reaction mixture containing an amide alcohol;

c) mixing tributyl phosphine and diisopropylazodicarboxylate to produce a reagent mixture;

d) adding the reagent mixture of step c) to the reaction mixture of step b); and e) isolating a compound of formula IA.

In a fourth embodiment of the instant invention, the process for synthesizing compounds of formula IB

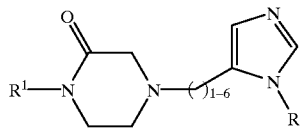

IB (where R is selected from unsubstituted or substituted aralkyl and $R^1$ is as defined above)

which comprises the steps of:

a) acylating an unsubstituted or substituted amine using an acylating agent of formula II

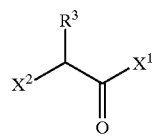

II (where $X^1$ is selected from halo, OH or unsubstituted or substituted $C_1$–$C_6$ alkoxy; $X^2$ is selected from halo or unsubstituted or substituted sulfonate and $R^3$ is as defined above) and an inorganic base compound;

b) adding an amino alcohol of formula III

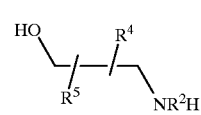

III (where $R^2$, $R^4$ and $R^5$ are as defined above) to produce a reaction mixture containing an amide alcohol of formula A

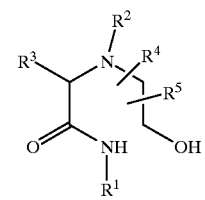

A (where $R^1$, $R^2$ $R^3$ $R^4$ and $R^5$ are as defined above);

c) adding a substituted chloroalkylimidazole salt and a non-protic solvent to the amide alcohol-containing reaction mixture;

d) adding a trialkylamine;

e) adding a phosphine and an azodicarboxylate; and f) isolating a compound of formula IB.

In a further embodiment of the instant invention, the process for synthesizing compounds of formula IC

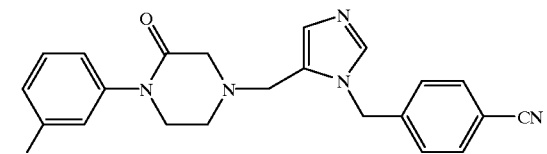

IC further comprises the steps of:

a) acylating 3-chloroaniline with chloroacetylchloride and aqueous potassium bicarbonate;

b) adding ethanolamine to produce a reaction mixture containing an amide alcohol;

c) combining the reaction mixture of step b) with 4-cyanobenzyl-chloromethylimidazole hydrochloride to produce a slurry;

d) treating the slurry with diisopropylethylamine;

e) adding tributyl phosphine and diethylazodicarboxylate; and f) isolating a compound of formula IC.

Compounds prepared using the process of the instant invention are useful as intermediates for making farnesyl-protein transferase inhibitors, such as those described in WO 96/30343 which was published on Oct. 3, 1996 and is herein incorporated by reference. Examples of compounds which can be made using the intermediates synthesized by the process of the instant invention include, but are not limited to, 5(S)-n-Butyl-1-(2,3-dimethylphenyl)-4-(4-imidazolylmethyl)-piperazin-2-one 5(S)-n-Butyl-4-[1-(4-cyanobenzyl)imidazol-5-ylmethyl]-1-(2,3-dimethylphenyl)piperazin-2-one 4-[1-(4-Cyanobenzyl)imidazol-5-ylmethyl]-1-(2,3-dimethylphenyl)-5(S)-(2-methoxyethyl)piperazin-2-one (S)-1-(3-Chlorophenyl)-4-[1-(4-cyanobenzyl)-5-imidazolylmethyl]-5-[2-(methanesulfonyl)ethyl]-2-piperazinone (S)-1-(3-Chlorophenyl)-4-[1-(4-cyanobenzyl)-5-imidazolylmethyl]-5-[2-(ethanesulfonyl)ethyl]-2-piperazinone (S)-1-(3-Chlorophenyl)-4-[1-(4-cyanobenzyl)-5-imidazolylmethyl]-5-[2-(ethanesulfonyl)methyl]-2-piperazinone (S)-1-(3-Chlorophenyl)-4-[1-(4-cyanobenzyl)-5-imidazolylmethyl]-5-[N-ethyl-2-acetamido]-2-piperazinone (±)-5-(2-Butynyl)-1-(3-chlorophenyl)-4-[1-(4-cyanobenzyl)-5-imidazolylmethyl]-2-piperazinone 1-(3-Chlorophenyl)-4-[1-(4-cyanobenzyl)-5-imidazolylmethyl]-2-piperazinone 5(S)-Butyl-4-[1-(4-cyanobenzyl-2-methyl)-5-imidazolylmethyl]-1-(2,3-dimethylphenyl)-piperazin-2-one 4-[1-(2-(4-Cyanophenyl)-2-propyl)-5-imidazolylmethyl]-1-(3-chlorophenyl)-5(S)-(2-methylsulfonylethyl)piperazin-2-one 5(S)-n-Butyl-4-[1-(4-cyanobenzyl)-5-imidazolylmethyl]-1-(2-methylphenyl)piperazin-2-one 4-[1-(4-Cyanobenzyl)-5-imidazolylmethyl]-5(S)-(2-fluoroethyl)-1-(3-chlorophenyl)piperazin-2-one 4-[3-(4-Cyanobenzyl)pyridin-4-yl]-1-(3-chlorophenyl)-5(S)-(2-methylsulfonylethyl)-piperazin-2-one 4-[5-(4-Cyanobenzyl)-1-imidazolylethyl]-1-(3-chlorophenyl)piperazin-2-one;

or the pharmaceutically acceptable salts, thereof.

As used herein, "alkyl" is intended to include both branched and straight-chain saturated aliphatic hydrocarbon groups having 1 to 6 carbon atoms, unless otherwise specified; "alkoxy" represents an alkyl group of 1 to 6 carbon atoms, unless otherwise indicated, attached through an oxygen bridge. "Halogen" or "halo" as used herein means fluoro, chloro, bromo or iodo.

As used herein, "aryl", and the "aryl" part of aryloxy, is intended to mean any stable monocyclic or bicyclic carbon ring of up to 7 members in each ring, wherein at least one ring is aromatic. Examples of monocyclic or bicyclic aryl elements include phenyl, naphthyl, tetrahydronaphthyl, indanyl, biphenyl, phenanthryl, anthryl or acenaphthyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of monocyclic and bicyclic heteroaryl elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein, "aralkyl" is intended to mean an aryl moiety, as defined above, attached through a $C_1$–$C_6$ alkyl linker, where alkyl is defined above. Examples of aralkyls inlcude, but are not limited to, benzyl, naphthylmethyl and phenylpropyl.

As used herein, "heteroaralkyl" is intended to mean a heteroalkyl moiety, as defined above, attached through a $C_1$–$C_6$ alkyl linker, where alkyl is defined above. Examples of heteroaralkyls include, but are not limited to, 2-pyridylmethyl, 2-imidazolylethyl, 2-quinolinylmethyl, 2-imidazolylmethyl and the like.

As used herein, the terms "substituted $C_1$–$C_6$ alkyl", "substituted —$(CH_2)_{1-6}$—", and "substituted $C_1$–$C_6$ alkoxy" are intended to include the branch or straight-chain alkyl group of the specified number of carbon atoms, wherein the carbon atoms may be substituted with F, Cl, Br, $CF_3$, $N_3$, $NO_2$, $NH_2$, oxo, —OH, —O($C_1$–$C_6$ alkyl), $S(O)_{0-2}$, ($C_1$–$C_6$ alkyl)$S(O)_{0-2}$—, ($C_1$–$C_6$ alkyl)$S(O)_{0-2}$($C_1$–$C_6$ alkyl)—, $C_3$–$C_{10}$ cycloalkyl, $C_2$–$C_6$ alkenyl, $C_2$–$C_6$ alkynyl, —C(O)NH, ($C_1$–$C_6$ alkyl)C(O)NH—, $H_2N$—C(NH)—, ($C_1$–$C_6$ alkyl)C(O)—, —O($C_1$–$C_6$ alkyl)$CF_3$, ($C_1$–$C_6$ alkyl)OC(O)—, ($C_1$–$C_6$ alkyl)O($C_1$–$C_6$ alkyl)—, ($C_1$–$C_6$ alkyl)C(O)$_2$($C_1$–$C_6$ alkyl)—, ($C_1$–$C_6$ alkyl)OC(O)NH—, aryl, benzyl, heteroaryl, halo-aryl, halo-benzyl, halo-heteroaryl, cyano-aryl, cyano-benzyl and cyano-heteroaryl.

As used herein, the terms "substituted aryl", "substituted heteroaryl", "substituted aralkyl", "substituted heteroaralkyl" are intended to include the cyclic group containing from 1 to 3 substituents in addition to the point of attachment to the rest of the compound. Such substitutents are preferably selected from the group which includes but is not limited to F, Cl, Br, $CF_3$, $NH_2$, $N(C_1$–$C_6$ alkyl)$_2$, $NO_2$, CN, $N_3$, $C_1$–$C_{20}$ alkyl, $C_1$–$C_6$ alkoxy, —OH, —O($C_1$–$C_6$ alkyl), $S(O)_{0-2}$, ($C_1$–$C_6$ alkyl)$S(O)_{0-2}$—, ($C_1$–$C_6$ alkyl)$S(O)_{0-2}$($C_1$–$C_6$ alkyl)—, ($C_1$–$C_6$ alkyl)C(O)NH—, $H_2N$—C(NH)—, ($C_1$–$C_6$ alkyl)C(O)—, ($C_1$–$C_6$ alkyl)OC(O)—, ($C_1$–$C_6$ alkyl)O($C_1$–$C_6$ alkyl)—, ($C_1$–$C_6$ alkyl)C(O)$_2$($C_1$–$C_6$ alkyl)—, ($C_1$–$C_6$ alkyl)OC(O)NH—, aryl, aralkyl, heteroaryl, heteroaralkyl, halo-aryl, halo-aralkyl, halo-heteroaryl, halo-heteroaralkyl, cyano-aryl, cyano-aralkyl, cyano-heteroaryl and cyano-heteroaralkyl.

As used herein, the term "substituted sulfonate" is intended to include sulfonates such as mesylate, tosylate and brosylate which are substituted with a halo-aryl or an unsubstituted or substituted $C_1$–$C_6$ alkyl.

Preferably, $R^1$ of formula I is selected from unsubstituted or substituted aryl. More preferably, $R^1$ is substituted aryl, wherein the substituents are selected from halo, $CF_3$, $NH_2$, CN, $C_1$–$C_{20}$ alkyl, —O($C_1$–$C_6$ alkyl), ($C_1$–$C_6$ alkyl)C(O)NH—, or $NO_2$. Most preferably, $R^1$ is 3-chlorophenyl.

Preferably, $R^2$ of formula I is selected from hydrogen, unsubstituted or substituted heteroaryl, unsubstituted or substituted aralkyl, or unsubstituted or substituted heteroaralkyl. More preferably, $R^2$ is hydrogen or a substituted heteroaralkyl. Most preferably, $R^2$ is hydrogen or 1-cyanobenzyl-5-imidazolylmethyl.

Preferably, $R^3$, $R^4$ and $R^5$ of formula I are independently selected from H, unsubstituted or substituted aryl, unsubstituted or substituted heteroaryl, unsubstituted or substituted $C_1$–$C_6$ alkyl or $C_1$–$C_6$ alkynyl. More preferably, $R^3$, $R^4$ and $R^5$ are independently selected from H or unsubstituted or substituted $C1$-$C_6$ alkyl. Most preferably, $R^3$, $R^4$ and $R^5$ are hydrogen.

Abbreviations used throughout the specification include:

| | |
|---|---|
| ACN | acetonitrile |
| $Ac_2O$ | acetic anhydride; |
| Boc | t-Butoxycarbonyl; |
| Cbz | Carbobenzyloxy; |
| DBU | 1,8-diazabicyclo[5.4.0]undec-7-ene; |
| DEAD | diethylazodicarboxylate |
| DIAD | diisopropylazodicarboxylate |
| DIEA | diisopropylethylamine |
| DPAD | dipiperidineazodicarbonyl |
| DMAP | 4-Dimethylaminopyridine; |
| DME | 1,2-Dimethoxyethane; |
| DMF | N,N-Dimethylformamide; |
| EDC | 1-(3-dimethylaminopropyl)-3-ethyl-carbodiimide-hydrochloride; |
| $Et_3N$ | Triethylamine; |
| EtOAc | Ethyl acetate; |
| FAB | Fast atom bombardment; |
| HOBT | 1-Hydroxybenzotriazole hydrate; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MsCl | Methanesulfonyl chloride; |
| MTBE | methyl-t-butyl-ether |
| NaHMDS | Sodium bis(trimethylsilyl)amide; |
| Py | Pyridine; |
| TFA | Trifluoroacetic acid; |
| THF | Tetrahydrofuran. |

The compounds synthesized by the invention are prepared by employing reactions as shown in Scheme 1.

These reactions may be employed in a linear sequence to provide the compounds of the formula I or they may be used to synthesize fragments which are subsequently joined by the reductive alkylation or acylation reactions described in the Scheme.

SCHEME 1

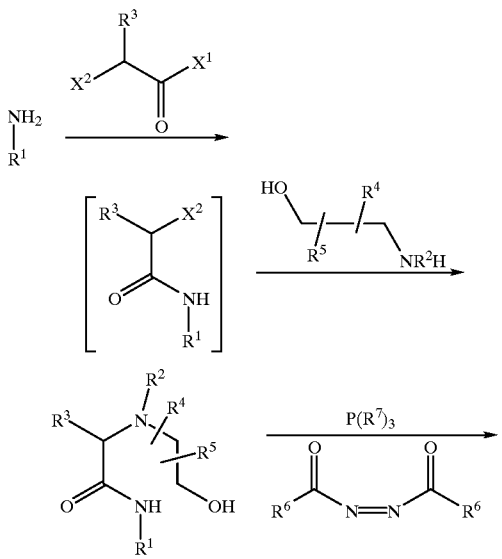

-continued

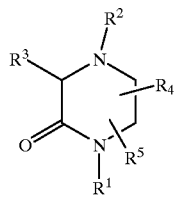

where
$X^1$ is selected from halo, OH or unsubstituted or substituted $C_1$–$C_6$ alkoxy;
$X^2$ is selected from halo or unsubstituted or substituted sulfonate;
$R^1$ represents H, unsubstituted or substituted $C_1$–$C_6$ alkyl, unsubstituted or substituted aryl, unsubstituted or substituted heteroaryl, —$R^aC(O)OR$, or —$R^aSR$;
R is independently selected from unsubstituted or substituted $C_1$–$C_6$ alkyl, unsubstituted or substituted aryl, or unsubstituted or substituted aralkyl;
$R^a$ is independently selected from unsubstituted or substituted —$(CH_2)_{1-6}$—, unsubstituted or substituted aryl, or unsubstituted or substituted aralkyl;
$R^2$, $R^3$, $R^4$ and $R^5$ in dependently represent H, unsubstituted or substituted $C_1$–$C_6$ alkyl; unsubstituted or substituted aryl, unsubstituted or substituted heteroaryl, unsubstituted or substituted aralkyl, unsubstituted or substituted heteroaralkyl, unsubstituted or substituted $C_1$–$C_6$ alkoxy, $C_1$–$C_6$ alkynyl, $CF_3$, and $OCF_3$;
$R^6$ independently represents OEt, O-i-Pr, O-t-Bu, pyrrolidine, piperidine, or dialkylamino; and
$R^7$ represents $C_1$–$C_6$ alkyl or phenyl.

The present invention relates to a process for the synthesis of substituted piperazinones via a Mitsunobu reaction. The first step in this process is acylation of an unsubstituted or substituted amine using an acylating agent of formula II

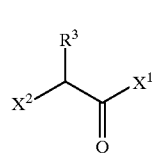

II (where $X^1$ is selected from halo, OH or unsubstituted or substituted $C_1$–$C_6$ alkoxy; $X^2$ is selected from halo or unsubstituted or substituted sulfonate and $R^3$ is as defined above) and a base compound. Types of unsubstituted or substituted amines that may be used include, but are not limited to, unsubstituted or substituted aryl-, heteroaryl- or $C_1$–$C_6$ alkylamines, ammonia, $H_2N$—$R^aC(O)OR$ and $H_2N$—$R^aSR$ (where $R^a$ and R are as defined above). Preferably, the unsubstituted or substituted amine is an aniline, unsubstituted or substituted. The substituted aniline may possess 1 to 5 substituents, wherein the substituents may include, but are not limited to, $C_1$–$C_6$ alkyl, $C_1$–$C_6$ alkoxy, aryloxy or halogen.

Types of acylating agents of Formula II that may be used include, but are not limited to, chloroacetyl chloride, bromoacetyl bromide, or a mixed system, such as bromoacetyl chloride. Additionally, the acylating agents of Formula II may include unsubstituted or substituted sulfonates, where the sulfonate is substituted with a $C_1$–$C_6$ alkyl or a halo-aryl. Examples of such substituted sulfonates include, but are not limited to, ethyl mesylate, bromophenyl tosylate, methyl brosylate, and the like.

The base compound utilized may be selected from an inorganic or organic base. Types of inorganic bases that might be used include, but are not limited to, bicarbonates, carbonates or hydroxides. Types of organic bases that might be employed include, but are not limited to, triethylamine, diisopropylethylamine, tributylamine, and the like. Preferably, an aqueous solution of an inorganic base is used. Types of solvents that may be used include, but are not limited to, non-protic solvents such as ethyl acetate, isopropylacetate, THF, MTBE, toluene, acetonitrile, DMF, and the like. The acylation may take place at a temperature range between about −20° C. to about 50° C. and a concentration of about 0.1 to about 2.0 M. The acylation is optimally run in a concentration of about 0.85 to about 1.1 M isopropylacetate, using about 1.8 equivalents of aqueous potassium bicarbonate at a temperature range of about 0° C. to about 5° C. with about 1.2 equivalents of chloroacetyl chloride.

Next, an amino alcohol of Formula III

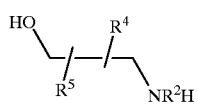

III (where $R^2$, $R^4$ and $R^5$ are as defined above) is added to produce a reaction mixture containing an amide alcohol of formula A. If an aqueous solution of an inorganic base is used in the acylation step, then the organic layer is separate from the aqueous layer, prior to the addition of the amino alcohol. Examples of amino alcohols of Formula III which may be used include, but are not limited to, ethanolamine, 2-amino-2-methyl-1-propanol, 1-hydroxy-1-methylaminohexane, N-methyl ethanolamine and the like.

In a second embodiment of the instant invention, the amino alcohol is added inversely. In this embodiment, the unsubstituted or substituted amine is acylated using an acylating agent, as previously described, to produce an acylated product. Then the acylated product is added to the amino alcohol of formula III to produce the reaction mixture containing an amide alcohol of formula A.

The reaction mixture produced from either the first or second embodiment is heated and aged for a specific amount of time. The amination is performed using one of the solvents mentioned above. Optimally, about 2.0 to about 10 equivalents of ethanolamine is used and the reaction mixture is heated to a temperature between about 40° C. to about 70° C., over about 20 to about 40 minutes and then aged for about 1 to about 5.0 hours.

In a further embodiment, water and a non-protic solvent are then added to the reaction mixture containing the amide alcohol of formula A to produce a biphasic reaction mixture, which is then agitated for about 10 to about 20 minutes at about 55° C. Optimally, the non-protic solvent is isopropyl acetate. The aqueous layer is separated from the organic layer. The organic layer is cooled to a temperature of about 35° C. to about 45° C., and seed is added to the organic layer, to produce a slurry. This slurry is cooled to a temperature of about −10° C. to 10° C. over about one hour and then aged for about 45 to about 90 minutes. The alcohol amide may be isolated by crystallization and filtration or by evaporative removal of the non-protic solvents from the organic layer.

Next, a phosphine is added to the reaction mixture containing the alcohol amide of formula A. Types of phosphines which may be used include, but are not limited to, trialkyl or triaryl phosphines. Examples of trialkyl or triaryl phosphines include, but are not limited to, tributyl phosphine, triphenyl phosphine, methyldiphenyl phosphine, and the like. Preferably, the phosphine is tributyl phosphine. A solvent, such as ethyl acetate or THF, may be used. A azodicarboxamide is then added over about 10 to about 20 minutes. Types of azodicarboxamides which may be used include, but are not limited to, amides in which the nitrogen moiety is dipyrrolidine, dipiperidine, dimorpholine, diphenylamine, diisopropylamine, diethylamine, dibutylamine, dimethylamine and the like. Examples of azodicarboxamides include, but are not limited to, dipyrrolidinylazodicarbonyl, dipiperidineazodicarbonyl, dimorpholinylazodicarbonyl, diphenylamineazodicarbonyl, diisopropylamineazodicarbonyl, diethylamineazodicarbonyl, dibutylamineazodicarbonyl, or dimethylamineazodicarbonyl. Preferably, dipiperidineazodicarbonyl (DPAD) is used. The mixture is then aged at about 0° C. to about 5° C., for about 15 to about 45 minutes. The mixture is then heated again to a temperature of about 20° C. to about 30° C. and additionally aged for about 14 to about 22 hours. The mixture was then cooled to a temperature of about 0° C. to about 10° C. and seeded with authentic material. Next, the mixture is treated with an organic or inorganic acid. Types of organic acids include, but are not limited to, acetic, propionic, TFA, MSA, citric acid, tartaric acid and the like. Types of inorganic acids include, but are not limited to, HCl, HBr, sulfuric and the like. Preferably, ethanolic HCl is added, over about 10 to about 30 minutes. The resulting slurry is then re-cooled to a temperature of about 5° C. to about 15° C. and aged for about 30 to about 90 minutes to produce a solid-containing mixture. The solids are then isolated to obtain a piperazinone salt of formula I.

In another embodiment of the invention, the alcohol amide of the amination step undergoes cyclodehydration. The alcohol amide is first slurried with a solvent, such as ethyl or isopropyl acetate, THF, chloroform, DMF or another non protic solvent, and a phosphine, as described previously, is added. Preferably, ethyl or isopropyl acetate and tributyl phosphine are used. The concentration range is about 0.1M to about 1.0M and the reagents are typically used in equal portions, from about 1.0 to about 2.0 equivalents, and preferably about 1.3 to about 1.4 equivalents each. If ethyl acetate is used, which is preferred when diisopropyl azodicarboxylate (DIAD) is used in the next step, then the piperazinone compound is obtained by directly adding an acid to the mixture after the addition of DIAD. Types of acids that may be utilized include, but are not limited to, HCl, HBr, HI, sulfuric, oxalic, tartaric, acetic, methanesulfonic, p-toluenesulfonic and the like. Most preferably, HCl is added after the addition of DIAD.

The slurry is then cooled to about −20° C. to about 50° C. and an azodicarboxylate is added. Types of azodicarboxylates that may used include, but are not limited to, diethyl, diisopropyl or di-t-butyl derivatives. Examples of azodicarboxylates include, but are not limited to, diethyl azodicarboxylate, diisopropyl azodicarboxylate or di-t-butyl azodicarboxylate. Preferably, diisopropylazodicarboxylate (DIAD) is used. The slurry is then heated to about 15° C. to about 25° C. so that the reaction mixture becomes homogeneous. This homogeneous mixture is then aged for about 45 to about 90 minutes at about 15° C. to about 25° C. The volatiles are evaporated and the residue is dissolved in an alcohol. The solution is then treated with ethanolic HCl and cooled to a temperature of about 0° C. to about 10° C. to form a slurry. This slurry is then aged for about 45 to about 90 minutes. The solids are then isolated to obtain a piperazinone compound of formula I.

In a third embodiment, the addition of the amino alcohol can also be done in the inverse mode, where the product of the acylation step is added to the amino alcohol instead. In one flask, a phosphine and an azodicarboxamide or azodicarboxylate, as previously described, are combined to produce a reagent mixture. Optimally, tributyl phosphine and DIAD are combined, while maintaining the temperature at <0° C. In a separate flask, an unsubstituted or substituted amine is acylated, using an acylating agent of formula II and a base compound, as previously described. Preferably, a substituted aniline is acylated using chloroacetyl chloride and aqueous potassium bicarbonate. An amino alcohol of formula III, as described previously, is added next to produce a reaction mixture. Preferably, ethanolamine is utilized. Then the reagent mixture from the first step is added to the reaction mixture and a compound of formula I is isolated.

In a fourth embodiment of the invention, the alcohol amide of the amination step is alkylated by combining it with a substituted chloroalkylimidazole salt and a non-protic solvent to form a slurry. Types of substituted chloroalkylimidazole salts which may be used include, but are not limited to, chloromethyl, chloroethyl or chloropropyl imidazoles substituted with unsubstituted or substituted $C_1$–$C_6$ alkyl, unsubstituted or substituted aryl, unsubstituted or substituted heteroaryl, unsubstituted or substituted aralkyl, or unsubstituted or substituted heteroaralkyl. Most preferably, the chloroalkylimidazole is a chloromethylimidazole, substituted with cyanobenzyl. Preferred solvents for this reaction include acetonitrile, alcohols, toluene, DMF, acetates, and the like Optimally, acetonitrile or an alcohol is used. The reaction is optimally run at about 0° C. to about 25° C. Higher temperatures lead to higher impurity levels. The slurry is then treated with a trialkylamine or an inorganic base, as previously described, over about 30 to about 90 minutes to produce a reaction mixture. Types of trialkylamines that may be used include, but are not limited to, triethylamine, diisopropylethylamine, tributylamine and the like. Preferably, diisopropylethylamine is used. The reaction mixture is then aged for about 15 to about 25 hours to form a slurry. Water is added dropwise, followed by cooling. The slurry is then aged for about 15 to about 90 minutes. The slurry is then filtered to isolate the solids, which are washed with chilled water and then dried to provide an imidazolyl amide alcohol. A phase transfer catalyst may be useful (tetra-alkylammonium iodide, sodium iodide and the like) in performing this reaction.

The imidazolyl amide alcohol then is combined with a phosphine, as described previously. A non-protic solvent, such as THF, and tributylphosphine, may be used. An azodicarboxylate, as previously described, is then added. Preferably, diethylazodicarboxylate is used. The reaction mixture is then aged for about 15 to about 60 minutes and a substituted piperazinone compound of formula I is isolated. Optimally, a 1-substituted aryl-4-[1-substituted-5-imidazolylmethyl] piperazinone is obtained.

EXAMPLES

Examples provided are intended to assist in a further understanding of the invention. Particular materials employed, species and conditions are intended to be further illustrative of the invention and not limitative of the reasonable scope thereof.

Example 1

Synthesis of the Amide Alcohol (1)

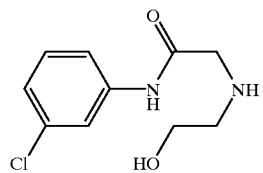

(1)

At 22° C., 3-chloroaniline (50.0 g) was combined with 460 ml isopropyl acetate and 20% aqueous potassium bicarbonate (72.5 g dissolved in 290 ml water). The biphasic mixture was cooled to 5° C. and chloroacetyl chloride (42 ml) was added dropwise over 30 minutes, keeping the internal temperature below 10° C. The reaction mixture was warmed to 22° C. over 30 min. The aqueous layer was removed at 22° C. and ethanolamine (92 ml) was added rapidly. The reaction mixture was warmed to 55° C. over 30 minutes and aged for 1 hour. At 55° C., 140 ml water was added with 30 ml isopropyl acetate to the reaction mixture. The biphasic reaction mixture was agitated for 15 minutes at 55° C. The layers were allowed to settle and the aqueous layer was removed. The organic layer was cooled to 45° C. and seed was added. The mixture was cooled to 0° C. over 1 hour and aged for 1 hour. The solids were filtered and washed with chilled isopropyl acetate (2×75 ml). The solids were dried in vacuo at 40° C. for 18 hours to provide about an 83.5% yield of the amide alcohol (1).

$^1$H NMR (300 MHz; DMSO-$d_6$) δ 7.85 (t, 1H 2.0 Hz), 7.52 (m, 1H), 7.32 (t, 1H, 8.0 Hz), 4.5–4.8 (br s, 1H), 3.47 (t, 1H, 5.5 Hz), 3.30 (s, 1H), 2.60 (t, 1H 5.0 Hz).

$^{13}$C NMR (75.4 MHz; DMSO-$d_6$) $δ_c$ 170.9, 140.1, 133.0, 130.3, 122.8 118.5, 117.5, 60.3, 52.7, 51.5.

Example 2

Synthesis of 1-(3-Chlorophenyl)-2-Piperazinone Hydrochloride with DPAD

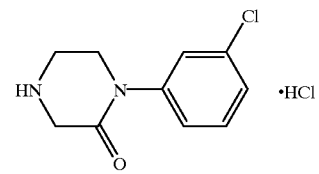

An amide alcohol, as described above in Example 1, was slurried with THF (37 ml) at 22° C., followed by the addition of tributyl phosphine (8.7 ml). The mixture was cooled to 0° C. and the DPAD was added in portions over 15 min. The slurry was aged at 0–5° C. for 30 minutes, warmed to 25° C. and aged for 18 hours. The reaction mixture was filtered and the cake was washed with THF (2×25 ml). The filtrate was concentrated in vacuo at <35° C. and combined with 50 ml of 2-propanol. The solution was cooled to 5° C., seeded with authentic material and treated with ethanol HCl (2.6 ml; 8.4M solution) dropwise over 20 min. The resulting slurry was recooled to 10° C. and aged for 1 hour. The solids were isolated and the cake and flask rinsed with chilled 2-propanol (2×10 ml). The product was dried in vacuo at 40° C. for 18 hours to provide about a 78% yield of the above-titled compound.

$^1$H NMR (300 MHz; DMSO-d$_6$) δ 10.24 (br s, 2H), 7.50–7.30 (m, 4H), 3.92 (t, 2H, 5.5 Hz), 3.84 (s, 2H), 3.51 (t, 5.5 Hz); $^{13}$C NMR (75.4 MHz; DMSO-d$_6$) δ$_c$ 162.1, 142.6, 132.9, 130.7, 127.0, 126.1, 124.54, 46.1, 44.9, 39.8.

Example 3

Synthesis of 1-(3-Chlorophenyl)-2-Piperazinone Hydrochloride with DIAD

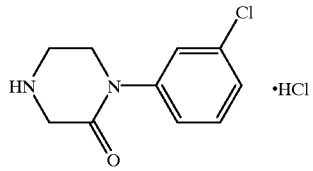

58 mL of EtOAc was charged to an N$_2$-purged flask. Tributylphosphine (28.3 mL, 113.8 mmol) was added, via syringe, and the solution was cooled to about −10° C. DIAD (22.4 mL, 113.8 mmol) was added dropwise over 30 minutes, maintaining the temperature at <0° C. The above mixture was cannulated into a slurry of an amide alcohol (20.0 g, 87.5 mmol), as described above in Example 1, in 117 mL EtOAc over 20 minutes, maintaining the temperature at <0° C. The reaction was warmed to room temperature over 25 minutes. 99% conversion was observed by LC assay. Water (0.55 mL) was then added, and the reaction was warmed to 40° C. The solution was seeded with 200 mg of authentic material, and 1.0 eq. HCl (4.0 N in abs. EtOH) was added dropwise over 2 hours. The slurry was cooled to 0° C. over 2 hours and aged at 0° C. for 1 hour. The mixture was filtered, and the cake was washed with chilled EtOAc (3×16 mL). The cake was dried in vacuo overnight at 40° C. to afford about a 77% yield of the above-titled compound.

Example 4

Synthesis of Imidazolyl Amide alcohol (2)

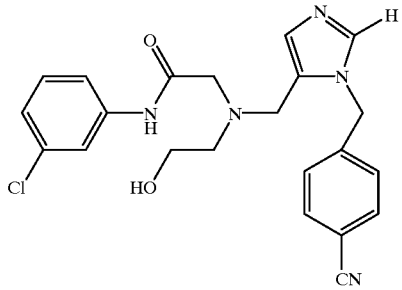

An amide alcohol, as described above in Example 1, was combined with 4-cyanobenzyl-chloromethylimidazole salt (4.5 g; 16.9 mmol) and acetonitrile (30 ml) at 20° C. The slurry was treated with diisopropylethylamine (6.8 ml; 39. mmol) dropwise over 1 hour. The reaction mixture was aged at 22° C. for 21 hours. Water (50 ml) was added dropwise followed by cooling to 2° C. The slurry was aged for 30 minutes and the solids isolated by filtration. The cake washed with chilled water (2×3 ml). The solids were dried in vacuo at 40° C. to provide about a 53% yield of the above-identified compound.

$^1$H NMR (300 MHz; DMSO-d$_6$): δ 7.76–7.66 (m, 3H), 7.39–7.27 (m, 2H), 7.21 (δ, 1H, 8.0 Hz), 7.10–7.05 (m, 1H), 6.93 (1H), 5.48 (s, 2H), 5.1–5.0 (m, 1H), 3.59 (s, 2H), 3.48–3.37 (br m, 3H)3.20 (s, 2H), 2.65–2.55 (br m, 2H); $^{13}$C NMR (75.4 MHz; DMSO-d$_6$) δ$_c$ 169.6, 143.5, 139.9, 139.1, 132.9, 132.5, 130.3, 129.4, 127.8, 127.2, 123.0, 118.5, 117.4, 110.1, 58.3, 57.0, 56.5, 47.5, 46.8.

Example 5

Synthesis of a 1-Substituted Aryl-4-[1-Substituted-5-Imidazolylmethyl] Piperazinone compound (3)

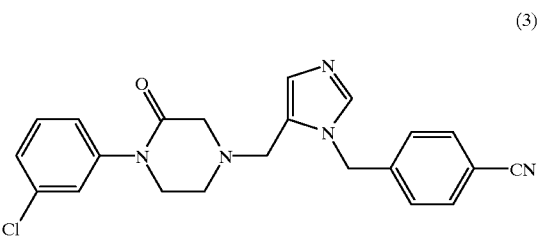

(3)

An imidazolyl amide alcohol (2) (1.0 g; 2.4 mmol), as described above in Example 4, was combined with THF (5.9 ml) and tributylphosphine (0.94 ml; 3.8 mmol) at 22° C. Diethylazodicarboxylate (0.6 ml; 3.8 mmol) was added dropwise and the reaction mixture aged at 22° C. for 30 min. Assay indicated a 98% yield of the above-identified compound.

$^{13}$C NMR (HCl salt; DMSO-d$_6$: 300 MHz): δ$_c$ 169.5, 143.5, 139.8, 139.1, 132.5, 132.3, 130.3, 129.4, 127.8, 127.2, 123.0, 118.5, 118.5, 117.4, 110.1, 58.3, 56.9, 56.5, 47.5, 46.8.

What is claimed is:

1. A process for synthesizing compounds of formula I

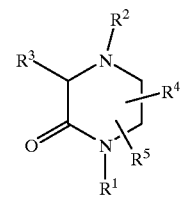

I wherein
R$^1$ is selected from
  a) H,
  b) unsubstituted or substituted C$_1$–C$_6$ alkyl,
  c) unsubstituted or substituted aryl,
  d) unsubstituted or substituted heteroaryl,
  e) —R$^a$C(O)OR, or
  f) —R$^a$SR;
R$^2$, R$^3$, R$^4$ and R$^5$ are independently selected from:
  a) H,
  b) unsubstituted or substituted C$_1$–C$_6$ alkyl;
  c) unsubstituted or substituted aryl,
  d) unsubstituted or substituted heteroaryl,
  e) unsubstituted or substituted aralkyl,
  f) unsubstituted or substituted heteroaralkyl,
  g) unsubstituted or substituted C$_1$–C$_6$ alkoxy,
  h) C$_1$–C$_6$ alkynyl;
  i) CF$_3$, and
  j) OCF$_3$;

R is independently selected from
  a) unsubstituted or substituted $C_1$–$C_6$ alkyl,
  b) unsubstituted or substituted aryl, or
  c) unsubstituted or substituted aralkyl;
$R^a$ is independently selected from:
  a) unsubstituted or substituted —$(CH_2)_{1-6}$—,
  b) unsubstituted or substituted aryl, or
  c) unsubstituted or substituted aralkyl;
or the pharmaceutically acceptable salts thereof;
which comprises the steps of:
  a) acylating an unsubstituted or substituted amine using an acylating agent of formula II $$\underset{X^2}{\overset{R^3}{\diagdown}} \underset{\underset{O}{\|}}{C} - X^1 \qquad \text{II}$$

(where $X^1$ is selected from halo, OH or unsubstituted or substituted $C_1$–$C_6$ alkoxy; $X^2$ is selected from halo or unsubstituted or substituted sulfonate and $R^3$ is as defined above) and a base compound;

b) adding an amino alcohol of formula III $$\text{HO}\underset{R^5}{\overset{R^4}{\diagdown}}\text{NR}^2\text{H} \qquad \text{III}$$

(where $R^2$, $R^4$ and $R^5$ are as defined above) to produce a reaction mixture containing an amide alcohol of formula A:

$$\text{A}$$

(where $R^1$, $R^2$ $R^3$ $R^4$ and $R^5$ are as defined above)
  c) adding a phosphine and adding an azodicarboxamide or an azodicarboxylate; and
  d) isolating a compound of the formula I.

2. The process of claim 1 wherein the unsubstituted or substituted amine is an aniline, unsubstituted or substituted with $C_1$–$C_6$ alkyl, $C_1$–$C_6$ alkoxy, aryloxy or halogen.

3. The process of claim 1 wherein the acylating agent of formula II comprises chloroacetyl chloride, bromoacetyl bromide, a mixed system or unsubstituted or substituted sulfonates.

4. The process of claim 1 wherein the base compound is an inorganic base which comprises bicarbonates, carbonates or hydroxides.

5. The process of claim 1 wherein the amino alcohol of formula III comprises ethanolamine, 2-amino-2-methyl-1-propanol, 1-hydroxy-1-methylaminohexane or N-methyl ethanolamine.

6. The process of claim 1 wherein the phosphine comprises tributyl phosphine, triphenyl phosphine, or methyldiphenyl phosphine.

7. The process of claim 1 wherein an azodicarboxamide is added in step c).

8. The process of claim 7 for synthesizing compounds of formula IA $$\text{IA}$$

which comprises the steps of:
  a) acylating 3-chloroaniline with chloroacetylchloride and aqueous potassium bicarbonate;
  b) adding ethanolamine to produce a reaction mixture containing an amide alcohol;
  c) adding tributyl phosphine and a dipiperidineazodicarbonyl; and
  d) isolating a compound of formula IA.

9. The process of claim 1 wherein, after the addition of the azodicarboxylate, the solution is aged at about 0° C. to about 5° C. for about 15 to about 45 minutes, heated again to a temperature of about 20° C. to about 30° C. and additionally aged for about 14 to about 22 hours.

10. The process of claim 1 wherein an azodicarboxylate is added in step c).

11. The process of claim 10 wherein the alcohol amide is first slurried with ethylacetate and then an azodicarboxylate is added, followed by direct addition of an acid to obtain a compound of formula I.

12. The process of claim 11 wherein the acid is HCl.

13. The process of claim 10 for synthesizing compounds of formula IA $$\text{IA}$$

which comprises the steps of:
  a) acylating 3-chloroaniline with chloroacetylchloride and aqueous potassium bicarbonate;
  b) adding ethanolamine to produce a reaction mixture containing an amide alcohol;
  c) adding tributyl phosphine and a diisopropylazodicarboxylate; and
  d) isolating a compound of formula IA.

14. The process of claim 13, wherein the compound of formula IA is isolated by directly adding an acid after the addition of the diisopropylazodicarboxylate.

15. The process of claim 14, wherein the acid is HCl.

16. The process of claim 1, wherein the temperature is between about 0° C. and about 5° C.

17. The process of claim 1 wherein the reaction mixture of step b) is heated to a temperature of about 40° C. to about 70° C., over about 20 to about 40 minutes and then aged for about 1 to about 5 hours.

18. A process for synthesizing compounds of formula I

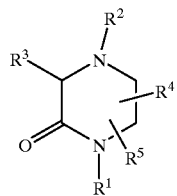

wherein
$R^1$ is selected from
  a) H,
  b) unsubstituted or substituted $C_1$–$C_6$ alkyl,
  c) unsubstituted or substituted aryl,
  d) unsubstituted or substituted heteroaryl,
  e) —$R^aC(O)OR$, or
  f) —$R^aSR$;
$R^2$, $R^3$, $R^4$ and $R^5$ are independently selected from:
  a) H,
  b) unsubstituted or substituted $C_1$–$C_6$ alkyl;
  c) unsubstituted or substituted aryl,
  d) unsubstituted or substituted heteroaryl,
  e) unsubstituted or substituted aralkyl,
  f) unsubstituted or substituted heteroaralkyl,
  g) unsubstituted or substituted $C_1$–$C_6$ alkoxy,
  h) $C_1$–$C_6$ alkynyl;
  i) $CF_3$, and
  j) $OCF_3$;
R is independently selected from
  a) unsubstituted or substituted $C_1$–$C_6$ alkyl,
  b) unsubstituted or substituted aryl, or
  c) unsubstituted or substituted aralkyl;
$R^a$ is independently selected from:
  a) unsubstituted or substituted —$(CH_2)_{1-6}$—,
  b) unsubstituted or substituted aryl, or
  c) unsubstituted or substituted aralkyl;
or the pharmaceutically acceptable salts thereof;
which comprises the steps of:
  a) acylating an unsubstituted or substituted amine using an acylating agent of formula II

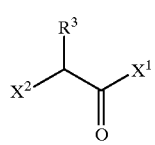

(where $X^1$ is selected from halo, OH or unsubstituted or substituted $C_1$–$C_6$ alkoxy; $X^2$ is selected from halo or unsubstituted or substituted sulfonate and $R^3$ is as defined above) and an inorganic base compound to produce an acylated product;
  b) adding the acylated product to an amino alcohol of formula III

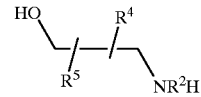

(where $R^2$, $R^4$ and $R^5$ are as defined above) to produce a reaction mixture containing an amide alcohol of formula A

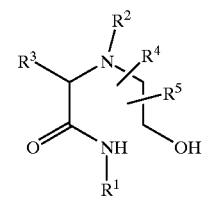

(where $R^1$, $R^2$ $R^3$ $R^4$ and $R^5$ are as defined above);
  c) adding a phosphine and adding an azodicarboxamide or an azodicarboxylate; and
  d) isolating a compound of the formula I.

19. The process of claim 18, wherein an azodicarboxamide is added in step c).

20. The process of claim 18, wherein an azodicarboxylate is added in step c).

21. A process for synthesizing compounds of formula I

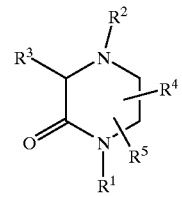

wherein
$R^1$ is selected from
  a) H,
  b) unsubstituted or substituted $C_1$–$C_6$ alkyl,
  c) unsubstituted or substituted aryl,
  d) unsubstituted or substituted heteroaryl,
  e) —$R^aC(O)OR$, or
  f) —$R^aSR$;
$R^2$, $R^3$, $R^4$ and $R^5$ are independently selected from:
  a) H,
  b) unsubstituted or substituted $C_1$–$C_6$ alkyl;
  c) unsubstituted or substituted aryl,
  d) unsubstituted or substituted heteroaryl,
  e) unsubstituted or substituted aralkyl,
  f) unsubstituted or substituted heteroaralkyl,
  g) unsubstituted or substituted $C_1$–$C_6$ alkoxy,
  h) $C_1$–$C_6$ alkynyl;
  i) $CF_3$, and
  j) $OCF_3$;
R is independently selected from
  a) unsubstituted or substituted $C_1$–$C_6$ alkyl,
  b) unsubstituted or substituted aryl, or
  c) unsubstituted or substituted aralkyl;

$R^a$ is independently selected from:
  a) unsubstituted or substituted —$(CH_2)_{1-6}$—;
  b) unsubstituted or substituted aryl, or
  c) unsubstituted or substituted aralkyl;
or the pharmaceutically acceptable salts thereof;
which comprises the steps of:
  a) acylating an unsubstituted or substituted amine using an acylating agent of formula II

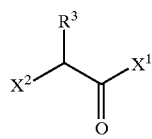

II (where $X^1$ is selected from halo, OH or unsubstituted or substituted $C_1$–$C_6$ alkoxy; $X^2$ is selected from halo or unsubstituted or substituted sulfonate and $R^3$ is as defined above) and an inorganic base compound to produce an acylated product;
  b) adding an amino alcohol of formula III

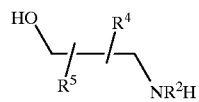

III (where $R^2$, $R^4$ and $R^5$ are as defined above) to the acylated product to produce a reaction mixture;
  c) mixing a phosphine and adding an azodicarboxylate or an azodicarboxamide to produce a reagent mixture;
  d) adding the reagent mixture from step c) to the reaction mixture of step b); and
  e) isolating a compound of formula I.

22. The process of claim 21, wherein an azodicarboxylate is used.

23. The process of claim 21, wherein an azodicarboxamide is used.

24. The process of claim 21, where in step b), the acylated product is added to the amino alcohol of formula III to produce a reaction mixture.

25. The process of claim 22, for synthesizing the compound of formula IA

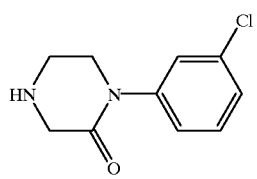

IA further comprises the steps of:
  a) acylating 3-chloroaniline with chloroacetylchloride and aqueous potassium bicarbonate;
  b) adding ethanolamine to produce a reaction mixture containing an amide alcohol;
  c) mixing tributyl phosphine and diisopropylazodicarboxylate to produce a reagent mixture;
  d) adding the reagent mixture of step c) to the reaction mixture of step b); and
  e) isolating the compound of formula IA.

26. A process for synthesizing compounds of formula IB

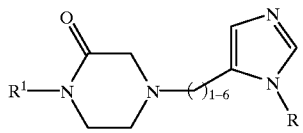

IB (where R is selected from unsubstituted or substituted aralkyl; $R^1$ is selected from H, unsubstituted or substituted $C_1$–$C_6$ alkyl, unsubstituted or substituted aryl, unsubstituted or substituted heteroaryl, —$R^aC(O)OR$ or —$R^aSR$; and $R^a$ is independently selected from unsubstituted or substituted —$(CH_2)_{1-6}$—, unsubstituted or substituted aryl, or unsubstituted or substituted aralkyl);
which comprises the steps of:
  a) acylating an unsubstituted or substituted amine using an acylating agent of formula II

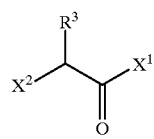

II (where $X^1$ is selected from halo, OH or unsubstituted or substituted $C_1$–$C_6$ alkoxy; $X^2$ is selected from halo or unsubstituted or substituted sulfonate and $R^3$ is as defined above) and an inorganic base compound;
  b) adding an amino alcohol of formula III

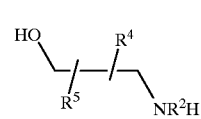

III (where $R^2$, $R^4$ and $R^5$ are as defined above) to produce a reaction mixture containing an amide alcohol;
  c) adding a substituted chloroalkylimidazole salt and a non-protic solvent to the amide alcohol-containing reaction mixture;
  d) adding a trialkylamine;
  e) adding a phosphine and an azodicarboxylate; and
  f) isolating a compound of formula IB.

27. The process of claim 26, wherein the substituted chloromethylimidazole salt is substituted with a substituent selected from the group: unsubstituted or substituted $C_1$–$C_6$ alkyl, unsubstituted or substituted aryl, unsubstituted or substituted heteroaryl, unsubstituted or substituted aralkyl, or unsubstituted or substituted heteroaralkyl.

28. The process of claim 26, wherein the substituted chloromethylimidazole salt is substituted with cyanobenzyl.

29. The process of claim 26, wherein the non-protic solvent comprises ethyl acetate, THF, MTBE, isopropyl acetate, toluene, DMF or acetonitrile.

30. The process of claim 26, wherein the trialkylamine comprises triethylamine, tributylamine, or diisopropylethylamine.

31. The process of claim 26, wherein the azodicarboxylate comprises diethylazodicarboxylate, diisopropylazodicarboxylate or di-t-butylazodicarboxylate.

32. The process of claim 31, for synthesizing compounds of formula IC

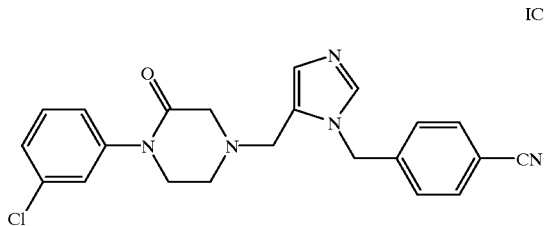

IC which comprises the steps of:
a) acylating 3-chloroaniline with chloroacetylchloride and aqueous potassium bicarbonate;
b) adding ethanolamine to produce a reaction mixture containing an amide alcohol;
c) combining the reaction mixture of step (b) with 4-cyanobenzyl-chloromethyl imidazole hydrochloride to produce a slurry;
d) treating the slurry with diisopropylethylamine;
e) adding tributyl phosphine and diethylazodicarboxylate; and
f) isolating a compound of formula IC.

33. The process of claim 26, wherein the acylation in step a) is conducted at a temperature of about −20° C. to about 50° C., the reaction mixture in step b) is heated to a temperature of about 50° C. to about 65° C., and the reaction in step c) is conducted at a temperature of about 0° C. to about 25° C.

* * * * *